Figure 4:
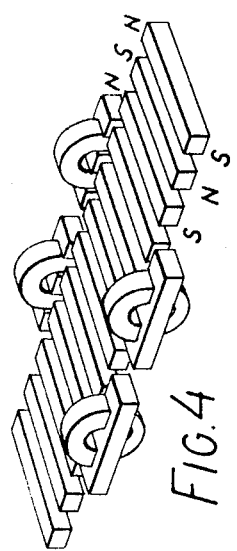

United States Patent [19]

Sloman

[11] 4,257,272
[45] Mar. 24, 1981

[54] ULTRASONIC APPARATUS

[75] Inventor: Anthony W. Sloman, Ditchling, England

[73] Assignee: E M I Limited, Hayes, England

[21] Appl. No.: 64,842

[22] Filed: Aug. 8, 1979

[51] Int. Cl.³ .......................................... G01N 29/00
[52] U.S. Cl. ...................................................... 73/633
[58] Field of Search ................ 73/618, 619, 620, 624, 73/633, 634

[56] References Cited

U.S. PATENT DOCUMENTS

| 3,023,611 | 3/1962 | Howry . | |
|---|---|---|---|
| 3,845,463 | 10/1974 | Timbs | 73/633 |
| 4,092,867 | 6/1978 | Matzuk | 73/619 |

*Primary Examiner*—James J. Gill
*Attorney, Agent, or Firm*—Fleit & Jacobson

[57] ABSTRACT

There have been proposed ultrasonic scanners in which a transducer is laterally scanned relative to a body known arrangements with lead screws for example can give rise to much vibration and have a high power requirement. It is proposed to scan with a linear motor drive. The scanning part including the transducer is put in an oil bath and the oil flow is balanced to act as a counterweight. The scanning part should, therefore, have neutral buoyancy, with the centers of gravity and buoyancy substantially coincident.

22 Claims, 10 Drawing Figures

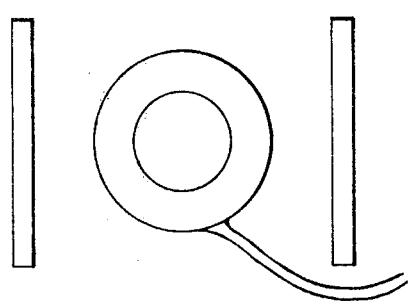
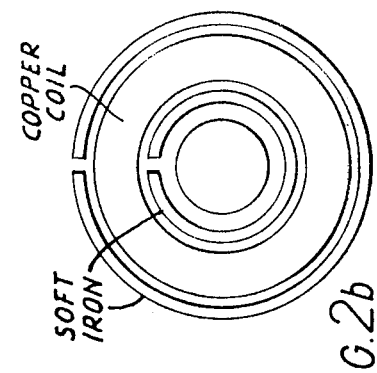
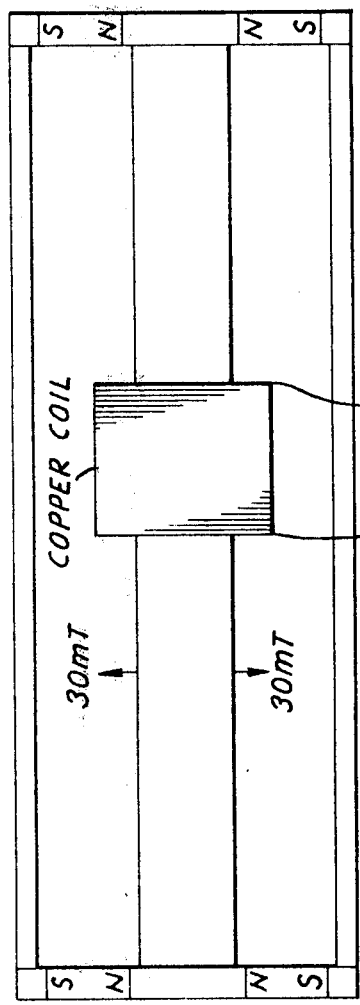
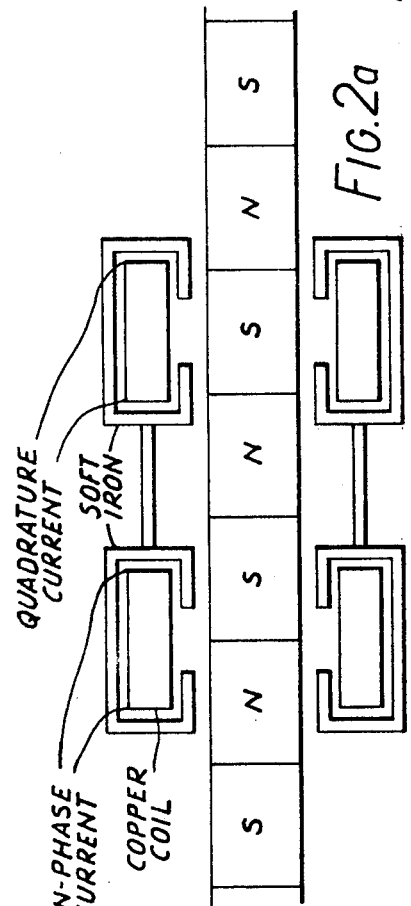
FIG.1
FIG.2a   FIG.2b

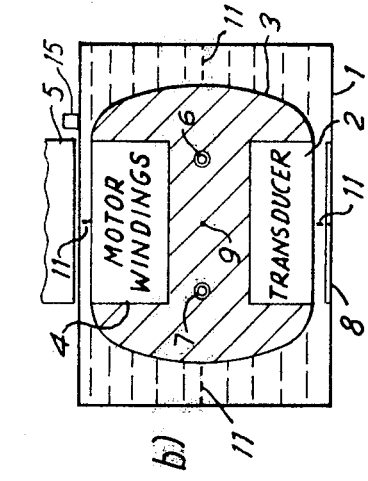
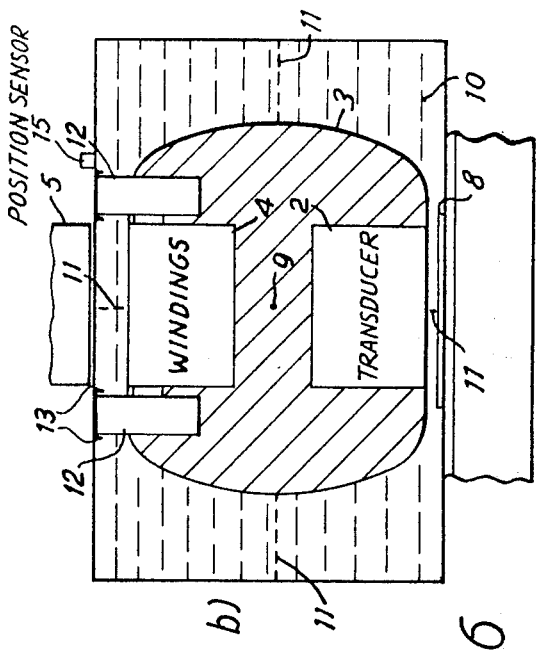
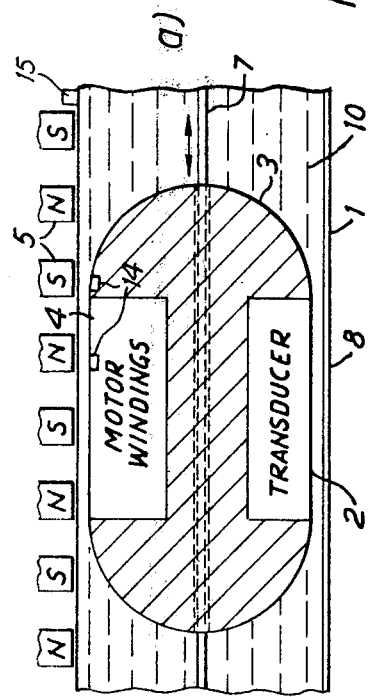
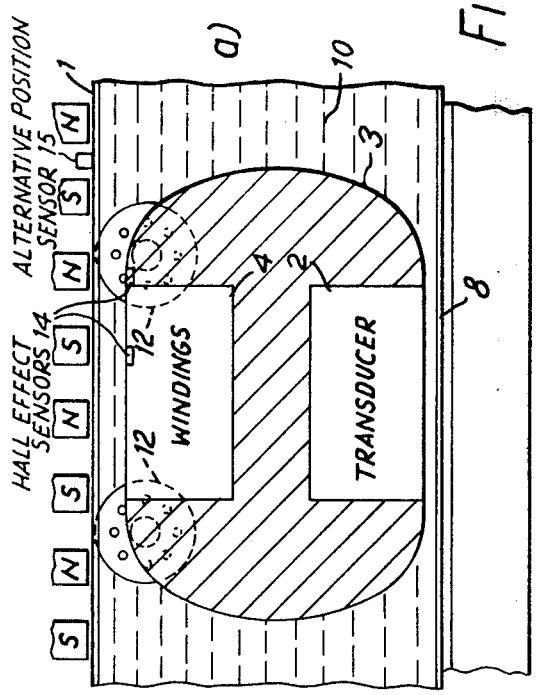
FIG. 5
FIG. 6

ULTRASONIC APPARATUS

This invention relates to ultrasonic examining apparatus in which a series of pulses of ultrasound are emitted along a series of parallel paths into a body to be examined and reflections from within the body are detected and processed to form an image of the body. The body may be a human body.

Known ultrasonic scanners include devices in which a transducer is rotated, either continuously or through a limited arc and the body is insonified along a plurality of radial paths. To provide a good ultrasonic transmission, the moving transducer may be in a water bath and a window in the bath used to couple the scanner to the body.

This rotating arrangement may be used to generate a rectilinear scan such as concerns this invention, by projecting the ultrasonic beam through a lens or by placing it at the focus of a parabolic mirror. Such devices are however bulky and heavy.

It has also been proposed to mechanically translate a transducer along a path perpendicular to the intended parallel ultrasound paths to achieve the rectilinear scan. An example of such a scanner can be seen in U.S. Pat. No. 3,023,611.

For a practical scanner a number of problems arise from such arrangements. It is desirable for medical use for the scanner to be light and compact so that it can be hand held. The transducer should be capable of accelerating and decelerating without dissipating excessive power in the scanning head and with a minimum of vibration. Furthermore the output should be capable of display as an optical image.

Continuously rotating transducers producing an arcuate scan are essentially free of vibration, required neither acceleration or deceleration, and can be spun fast enough to provide ultrasonic data at a rate which gives an apparently continuous optical image.

It is an object of this invention to provide an improved ultrasonic scanner to give a rectilinear scan.

According to one aspect of the invention there is provided an ultrasonic examination apparatus including: a liquid filled scanning head; an ultrasonic transducer arrangement including at least one ultrasonic transducer, mounted in the scanning head to be immersed in the liquid; guide means adapted to allow the transducer arrangement to be capable of a translational scanning motion through the liquid; and drive means for causing a reciprocating translational movement of the transducer arrangement, wherein the density of the liquid and the means density of the transducer arrangement are chosen so that the transducer arrangement is neutrally buoyant in the liquid with the centre of gravity and centre of buoyancy thereof being substantially coincident.

According to another aspect of the invention there is provided an ultrasonic examination apparatus including: a liquid filled scanning head; an ultrasonic transducer arrangement which includes at least one ultrasonic transducer and which is mounted in the scanning head to be capable of a translational scanning motion in the liquid; and means for driving the transducer arrangement in a reciprocating translational motion, wherein the transducer arrangement is neutrally buoyant in the liquid.

Figure 3C:
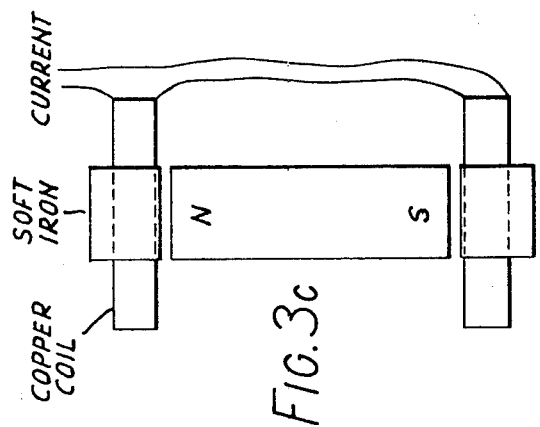
Figure 3B:
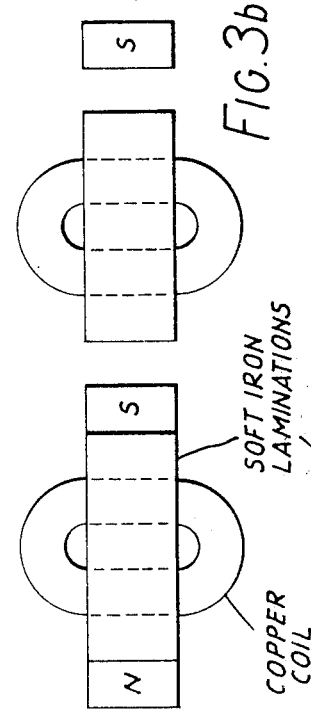
Figure 3A:
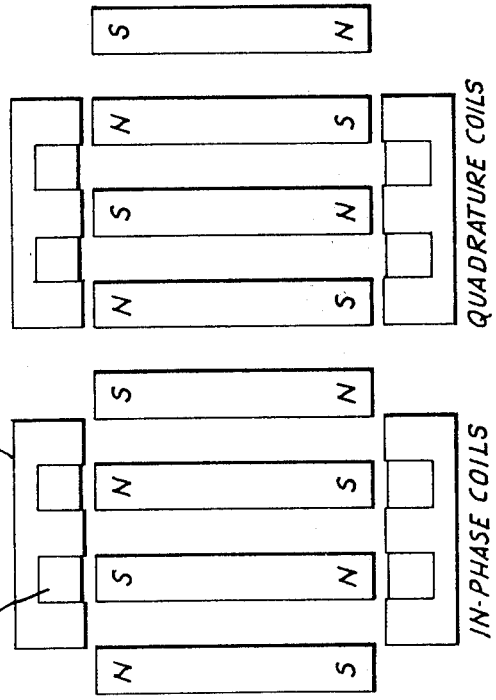
Figure 7:
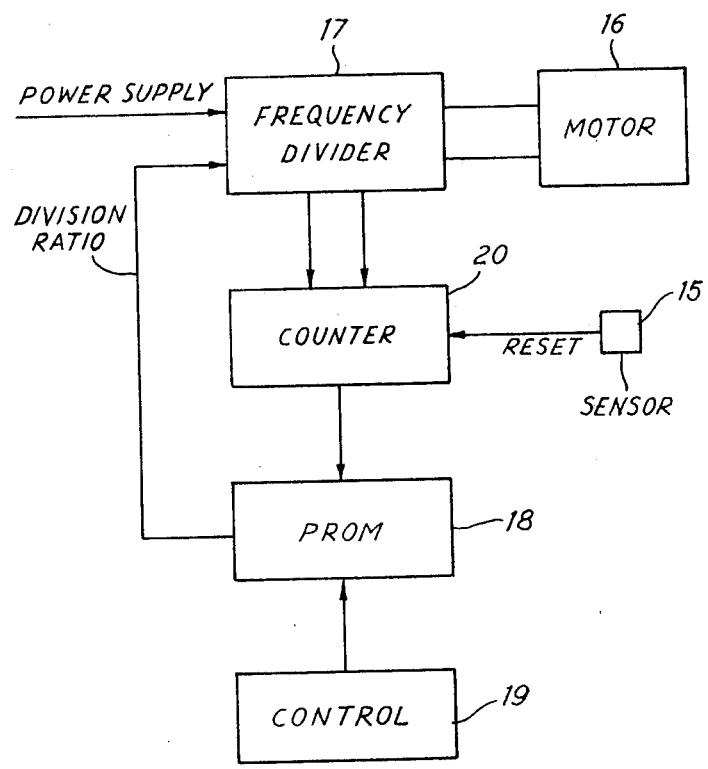

In order that the invention may be clearly understood and readily put into practice it will now be described by way of example with reference to the accompanying drawings, of which:

FIG. 1 shows a linear motor,

FIG. 2a and 2b show in plan and end elevation respectively an axial flux synchronous linear motor, FIGS. 3a, 3b and 3c show in plan side and end elevations respectively a transverse field linear motor, FIG. 4 shows the motor of FIG. 3 in perspective view, FIG. 5 shows an example of the transducer arrangement, FIG. 6 shows another example of the transducer arrangement and FIG. 7 shows a block diagram of a drive control circuit.

The invention consists of a scanning head filled with liquid (generally oil) in which the ultrasonic transducer is translated backwards and forwards, preferably by a linear synchronous motor.

An important feature of this invention is that of making the moving carriage carrying the transducer neutrally buoyant in an oil-bath, with its centre of gravity coincident with its centre of buoyancy, so that the displaced oil then becomes a perfect counter-weight, cancelling any external translational forces, and vibration is reduced. By channelling the oil flow correctly, external torques can also be cancelled. The oil return flow is then arranged to be symmetrical. Spring buffers are used to reverse the direction of scan so that the kinetic energy of the moving carriage is absorbed and restored, an effect which would otherwise have to be achieved through the linear motor windings; since the linear motor is less than perfectly efficient a portion of this energy would manifest itself as waste heat. The spring buffers are more efficient.

The ultrasonic data from a rectilinear scanner such as that of this invention may be displayed directly as an optical image on a standard television monitor; the information derived from one ultrasonic pulse can be made to correspond to a horizontal or vertical line of the television image without an elaborate scan converter.

The ultrasonic information derived from a rotating scanner, however, must be displayed directly on a specialised and expensive electronic display tube, or converted to standard TV format by an elaborate and expensive scan converter which forms the individual lines of the TV image from data derived from a variable number of ultrasonic pulses.

As mentioned hereinbefore, scanning assemblies are known in which the ultrasonic beam generated by a rotating transducer is redirected by a mirror or lens to produce a rectilinear scan, which could be displayed on a standard television set. This advantage is outweighed by the disadvantages attendant on the size of the ultrasonic optics. Such devices cannot readily be hand-held.

The transducer is preferably translated by a linear motor, which is shown in its simplest form in FIG. 1. A linear motor drive provides the advantages of mechanical simplicity, compactness and lightness. It is desirable to use a synchronous linear motor which provides the further advantage that the array of magnets, or coils, in the starter forms a position reference and the position of the motor is determined by the phase rather then by the voltage, of the AC drive to the motor: this is analogous to using a stepping motor to drive a rotary transducer. The position can be detected directly by using a pair of Hall-effect sensors mounted on the carriage. These sensors provide an indication of speed and direction of motion, as well as allowing the carriage to be driven with maximum efficiency as a form of brushless D.C. motor. However as an alternative the carriage may be run open loop, using a single stationary sensor at one end of the scan to check that the carriage is where it is expected to be in each scan.

A useful motor for use with this invention calls for magnetic flux paths of the order of 1 cm long or less; otherwise the mass of magnet and soft-iron flux path becomes substantial. The motor should also have both in-phase and quadrature coils, otherwise the direction of scan is indeterminate, the motor may not start at all, and "cogging", that is velocity variations, may be excessive. Several well known forms of linear motor may be used to drive the scanning carriage. These include an axial flux device which is shown in plan and elevation in FIG. 2a and FIG. 2b respectively and a transverse flux motor as shown in plan, side and end elevations in FIGS. 3a, b and c respectively and in a perspective view in FIG. 4.

It should be noted that the feature of the invention of achieving neutral buoyancy of the transducer in an oil bath is particularly beneficial in providing a well balanced and vibration free scanner. It is not limited to scanning induced by a linear motor but is particularly suited to such a scanner.

The linear motor offers the major advantage of simplicity, since carriage and motor form the one irreducible moving part. The inertia of the moving parts is thus minimised, and the synchronous linear motor proposed offers a relatively fast and well controlled scan.

The linear motor may not be as cheap as a conventional motor which would be an alternative. On the other hand, the linear motor replaces not only the conventional motor but also its drive train and can give a cheaper scanning head.

A basic linear motor for a low cost rectilinear scanner may be built into a light, small and simple scanning carriage, capable of only 4.5 scans per second of an 18 cm path. The motor design is preferably optimised for 2.25 MHz transducers, and reduced scans for 3.5 and 5 MHz transducers can then be produced by dividing down the motor drive frequency.

The more advanced high frequency (5 MHz or above) real-time rectilinear scanner can use the same machine electronics, apart from a redesigned image store to accept the higher scanning rate. The short range and low mass of a 5 MHz transducer means that real-time scan rates (10 scan/sec or higher) can be achieved over an acceptable shorter scan (9 cm) with the same sort of force and power needed to drive a 2.25 MHz transducer at 4.5 scan/sec over 18 cm, so that the same linear motor may be used.

Power dissipation is a significant factor to be considered. The power required to accelerate and decelerate the scanning carriage goes up as the cube of the scan rate, while if the carriage is driven by a motor mounted in the scanning head, the waste heat to be dissipated in this hand-held assembly goes up as the fourth power of scan rate. It is preferable to limit the dissipation to less than 5 W.

Frictional losses due to the viscosity of the oil are relatively small; using 100 cP viscosity oil with the motor proposed they would amount to 0.2 W at 4.5 scan/sec for the 2.25 MHz scanner, increasing as the square of the scan rate until turbulence sets in, when dissipation increases as the cube.

FIG. 5 shows at (a) and (b) respectively side and end elevation cross sections of a transducer arrangement using the invention, mounted for translational movement in an oil filled container 1.

The transducer 2 is of known type, for example quartz or a piezo-electric polymer, and is mounted in a closed cell 3 opposing the face and windings 4 of the linear motor which, like the transducer are only shown as a block since they are of well known type. In this example the linerar motor is single sided and the stator 5 is disposed along the side of the container 1 facing the rotor face and at a suitable distance, typically 10 thousandths of an inch. The cell 3 is mounted on bearings, indicated in this example, as sliding bearings 6 on rods 7, to move as shown. The bearings space the cell and the transducer at a suitable distance, also typically 10 thousandths of an inch, from an ultrasonic window 8.

To achieve the desired result the cell and transducer and motor rotor are to be neutrally buoyant in the oil. The cell 3 is composed of a plastic foam of such a volume that the cell and contents displace their own mass of oil. The cell is shaped such that the centre of mass of the moving unit is substantially centrally placed in cross section at 9 and so that the oil 10 in container 1 can easily move past it. Another consideration is that the oil should be displaced symmetrically by the cell so that if one considers any plane defined by the centre of mass of the moving unit and the direction of movement the oil flow should be parallel to the plane. That is to say that considering a second plane at right angles to the direction of motion net mass transferred through this plane should be zero both above and below the first plane, thus eliminating any net torque. To this end any pair of oil ducts defined by the walls of the container and the surface of the cell and the first plane should have equal resistance to flow.

FIG. 6 shows in (a) and (b) the same views as FIG. 5 but of an improved arrangement. Since the motor is a single sided linear motor it will have a tendency to pull towards the stator 5. Thus the bearings can be as shown at 12 being ball race wheels which hold the cell the required distance from the stator. If desired they can run in tracks 13.

FIG. 6 also shows an ultrasonic stand-off to space the transducer from the body to aid in, for example, skin imaging and to protect the ultrasonic window. In other respects it is much like the arrangement of FIG. 5 especially with regard to the feature of neutral buoyancy and oil flow.

Also shown in FIGS. 5 and 6 are the pair of Hall effect sensors 14 and the alternative of a stationary sensor 15. The Hall effect sensors 14 are spaced so as to give quadrature outputs as the field is sensed and give accurate positioning. The sensor 15 may take any suitable form to show the presence of the carriage, for example an optical sensor comprising light source and photocell. As both forms of sensors are well known they have only been indicated as blocks.

FIG. 7 illustrates, in block diagrammatic form, a suitable variable frequency drive arrangement for the system. The linear motor, indicated at 16, is driven by a suitable power supply, not shown, via a frequency divider 17. The frequency divider 17 is controlled by a Programmable read only memory (PROM) 18 which is preprogrammed to appropriate control functions by a suitable control unit 19.

An up/down counter 20 is driven by the same waveform as the motor 16, and acts as a carriage position indicator, reset from time to time by a sensor (statonary sensor 15). The output of the up/down counter 20 controls PROM 19 which, as programmed, then changes the division ratio of divider 17 to alter the motor drive frequency.

If, for any reason, the carriage drops out of synchronism and becomes "lost" this may be indicated by the persisting absence of the check output (over more than one scan, say). The PROM output can then be jammed high when the output of 20 reaches a predetermined level to ensure that the motor is driven in the stepping mode towards the stationary sensor. The condition may also be forced when the machine is turned on, and can be used to select particular lines in the picture for T-M mode examinations.

Alternative drive arrangements may be devised as desired for the transducer arrangement of this invention.

What I claim is:

1. An ultrasonic examination apparatus including: a liquid filled scanning head; an ultrasonic transducer arrangement including at least one ultrasonic transducer, mounted in the scanning head to be immersed in the liquid; guide means adapted to allow the transducer arrangement to be capable of a translational scanning motion through the liquid; and drive means for causing a reciprocating translational movement of the transducer arrangement, wherein the density of the liquid and the mean density of the transducer arrangement are chosen so that the transducer arrangement is neutrally buoyant in the liquid with the centre of gravity and centre of buoyancy thereof being substantially coincident.

2. An apparatus according to claim 1 in which the liquid is oil.

3. An apparatus according to claim 1 in which the at least one transducer arrangement comprises a flotation cell containing the ultrasonic transducer.

4. An apparatus according to claim 3 in which the cell is made of a plastic foam material and the transducer is placed at the edge thereof arranged such that the emitted ultrasonic energy is not shielded by foam material.

5. An apparatus according to either of claims 3 and 4 in which the centre of mass of the cell, including parts contained therein is substantially centrally placed in cross section perpendicular to the direction of motion.

6. An apparatus according to claim 1 in which the drive means comprises a linear electric motor.

7. An apparatus according to claim 6 in which the motor is a synchronous linear motor.

8. An apparatus according to claim 6 in which the transducer arrangement comprises a flotation cell containing an ultrasonic transducer and the rotor of the linear motor having their combined mass substantially uniformly distributed about the centre of buoyancy.

9. An apparatus according to claim 8 in which the flotation cell is made of a plastic foam material.

10. An apparatus according to claim 1 in which the at least one transducer is a quartz piezo-electric transducer.

11. An apparatus according to claim 1 in which at least one transducer is a piezo-electric polymer.

12. An apparatus according to claim 1 in which the transducer arrangement is mounted in the scanning head such that, during motion, displaced liquid moves past the head substantially symmetrically so as not to impose out of balance forces thereon.

13. An apparatus according to claim 12 in which any pair of effective liquid ducts on opposite sides of the transducer arrangement have substantially equal resistance to liquid flow.

14. An apparatus according to claim 1 in which the guide means comprises at least one bearing cooperating with and sliding on at least one rod member.

15. An apparatus according to claim 1 in which the guide means comprises a plurality of wheels in contact with at least one wall of the scanning head.

16. An apparatus according to claim 1 including at least one position sensor determining the presence of the transducing arrangement at least one position in its range of motion.

17. An apparatus according to claim 16 in which the at least one position sensor is mounted on the transducer arrangement to share in the motion thereof.

18. An apparatus according to claim 17 in which the drive means is a linear electric motor and the at least one position sensor is a pair of Hall effect sensors sensing the magnetic field thereof.

19. An ultrasonic examination apparatus including: a liquid filled scanning head; an ultrasonic transducer arrangement which includes at least one ultrasonic transducer and which is mounted in the scanning head to be capable of a translational scanning motion in the liquid; and means for driving the transducer arrangement in a reciprocating translational motion, wherein the transducer arrangement is neutrally buoyant in the liquid.

20. An ultrasonic examination apparatus including: a liquid filled scanning head; a flotation cell mounted for translational movement inside the scanning head; at least one ultrasonic transducer device mounted in the flotation cell; and means for driving the flotation cell in a reciprocating translational motion to scan ultrasonic energy emitted by the device in relation to a body in contact with the scanning head, wherein the flotation cell and components included therein have, in total, neutral buoyancy in said liquid.

21. An apparatus according to claim 20 in which the liquid flows past the flotation cell during said said motion to form an effective countermass to the motion.

22. A medical ultrasonic examination apparatus for examining a body, the apparatus including: an oil filled scanning head adapted to be placed in contact with the body; a flotation cell, including at least one ultrasonic transucer device, mounted in the scanning head to be immersed in the oil; guide means adapted to allow the flotation cell to be capable of a translational scanning motion through the oil; and drive means for causing a reciprocating translational motion of the flotation cell, and therefore the at least one transducer, relative to the body, wherein the flotation cell, including components associated therewith, is neutrally buoyant in the oil.

* * * * *

UNITED STATES PATENT AND TRADEMARK OFFICE
CERTIFICATE OF CORRECTION

PATENT NO. : 4,257,272
DATED : March 24, 1981
INVENTOR(S) : ANTHONY W. SLOMAN

It is certified that error appears in the above—identified patent and that said Letters Patent is hereby corrected as shown below:

On the title page, insert

-- (30)  Foreign Application Priority Data

August 11, 1978   GREAT BRITAIN..........33138/78 --

Signed and Sealed this

First Day of September 1981

[SEAL]

Attest:

Attesting Officer

GERALD J. MOSSINGHOFF

Commissioner of Patents and Trademarks